United States Patent
Fabritius

(10) Patent No.: US 12,228,998 B2
(45) Date of Patent: *Feb. 18, 2025

(54) DIAGNOSTIC TEST PRIORITIZATION BASED ON ACCUMULATED DIAGNOSTIC REPORTS

(71) Applicant: BLANCCO TECHNOLOGY GROUP IP OY, Joensuu (FI)

(72) Inventor: Mikko Fabritius, Joensuu (FI)

(73) Assignee: BLANCCO TECHNOLOGY GROUP IP OY, Joensuu (FI)

(*) Notice: Subject to any disclaimer, the term of this patent is extended or adjusted under 35 U.S.C. 154(b) by 139 days.

This patent is subject to a terminal disclaimer.

(21) Appl. No.: 17/614,125

(22) PCT Filed: Apr. 14, 2020

(86) PCT No.: PCT/FI2020/050240
§ 371 (c)(1),
(2) Date: Nov. 24, 2021

(87) PCT Pub. No.: WO2020/240076
PCT Pub. Date: Dec. 3, 2020

(65) Prior Publication Data
US 2022/0229717 A1    Jul. 21, 2022

(30) Foreign Application Priority Data
May 27, 2019  (FI) .................................. 20195439

(51) Int. Cl.
*G06F 11/00*      (2006.01)
*G06F 11/07*      (2006.01)
(Continued)

(52) U.S. Cl.
CPC ...... *G06F 11/0769* (2013.01); *G06F 11/0748* (2013.01); *G06F 11/2294* (2013.01);
(Continued)

(58) Field of Classification Search
CPC ............ G06F 11/0769; G06F 11/0748; G06F 11/0787; G06F 11/2294; G06F 11/3452; G06F 11/3495
See application file for complete search history.

(56) References Cited

U.S. PATENT DOCUMENTS

| 6,338,148 B1 * | 1/2002 | Gillenwater | ........ G06F 11/2273 |
| | | | 714/25 |
| 8,135,997 B2 * | 3/2012 | Kim | .................... G06F 11/0769 |
| | | | 714/48 |

(Continued)

FOREIGN PATENT DOCUMENTS

| JP | 2001312375 A | 11/2001 |
| JP | 2009206850 A | 9/2009 |

(Continued)

OTHER PUBLICATIONS

International Preliminary Report on Patentability dated Nov. 16, 2021 (Nov. 16, 2021) issued on related international patent application PCT/FI2020/050240 by The International Bureau of WIPO.

(Continued)

*Primary Examiner* — Elmira Mehrmanesh
(74) *Attorney, Agent, or Firm* — DICKINSON WRIGHT PLLC

(57) ABSTRACT

According to an aspect, there is provided a method for guiding a user in diagnostic test selection. Initially, one or more diagnostic reports on each of a plurality of computing devices are maintained in a diagnostic report database. In response to receiving a first set of one or more device parameters characterizing a second computing device from a first computing device, a remote computing system compares the first set to a plurality of sets of device parameters maintained in the diagnostic report database to find one or more relevant diagnostic reports. The remote computing system predicts results of one or more diagnostic tests when (Continued)

performed on the second computing device based on results of one or more diagnostic tests in the one or more relevant diagnostic reports by using statistical analysis. The remote computing system sends results of the predicting to the first computing device.

19 Claims, 8 Drawing Sheets

(51) Int. Cl.
*G06F 11/22* (2006.01)
*G06F 11/34* (2006.01)
(52) U.S. Cl.
CPC ...... *G06F 11/3452* (2013.01); *G06F 11/3495* (2013.01); *G06F 11/0787* (2013.01)

(56) References Cited

U.S. PATENT DOCUMENTS

| | | | | |
|---|---|---|---|---|
| 8,997,061 | B1* | 3/2015 | Davison | G06F 11/3688 |
| | | | | 717/124 |
| 10,019,305 | B2* | 7/2018 | Aneja | G06F 11/0709 |
| 10,152,407 | B1* | 12/2018 | Zachesov | G06F 11/079 |
| 10,162,693 | B1* | 12/2018 | Contino | G06F 11/0742 |
| 10,291,498 | B1* | 5/2019 | Gailloux | H04W 4/00 |
| 2003/0005107 | A1 | 1/2003 | Dulberg et al. | |
| 2005/0005186 | A1* | 1/2005 | Goebel | G06Q 10/06 |
| | | | | 714/1 |
| 2006/0224537 | A1* | 10/2006 | Gonguet | H04L 41/0631 |
| | | | | 706/16 |
| 2007/0294001 | A1* | 12/2007 | Underdal | G06N 7/01 |
| | | | | 701/31.4 |
| 2008/0294423 | A1* | 11/2008 | Castellani | G06F 16/3329 |
| | | | | 704/4 |
| 2010/0125753 | A1* | 5/2010 | Gadher | G06F 11/008 |
| | | | | 714/26 |
| 2014/0024348 | A1* | 1/2014 | Hurst | H04M 3/5232 |
| | | | | 455/414.1 |
| 2015/0052122 | A1* | 2/2015 | Landry | G06F 16/248 |
| | | | | 707/723 |
| 2015/0067422 | A1* | 3/2015 | Hamilton | G06F 11/24 |
| | | | | 714/724 |
| 2015/0082097 | A1* | 3/2015 | Brewer | G06F 11/3428 |
| | | | | 714/47.1 |
| 2015/0347282 | A1* | 12/2015 | Wingfors | G06F 11/3664 |
| | | | | 717/124 |
| 2021/0049063 | A1* | 2/2021 | Reed | G06F 11/0793 |
| 2021/0248618 | A1* | 8/2021 | Ionescu | G06Q 30/016 |
| 2022/0342738 | A1* | 10/2022 | Samuel | G06N 20/00 |

FOREIGN PATENT DOCUMENTS

| | | |
|---|---|---|
| WO | WO0159972 | 8/2001 |
| WO | 2008120552 | 7/2010 |

OTHER PUBLICATIONS

Notice of Reasons for Refusal / Japanese Office Action dated Mar. 18, 2024 , (Mar. 18, 2024), 4 pages, issued on related Japanese patent application 2021-570437, by the Japanese Patent Office.
Decision to Grant a Patent issued Jul. 30, 2024 (Jul. 30, 2024), 5 pages, issued on related Japanese Patent Application 2021-570437 by the Japanese Patent Office.

\* cited by examiner

DIAGNOSTIC TEST PRIORITIZATION BASED ON ACCUMULATED DIAGNOSTIC REPORTS

CROSS REFERENCE TO RELATED APPLICATIONS

This application is a U.S. National Phase patent application of and claims priority to PCT Application No. PCT/FI2020/050240, filed Apr. 14, 2020, which claims priority to and the benefit of Finland Patent Application 20195439 filed on May 27, 2019, each of the foregoing applications being fully incorporated herein by reference for all purposes.

FIELD OF THE INVENTION

The present invention relates to diagnosing computing devices and particularly to providing means for performing diagnostic test prioritization for a computing device.

BACKGROUND

The following background description art may include insights, discoveries, understandings or disclosures, or associations together with disclosures not known to the relevant art prior to the present invention but provided by the present disclosure. Some such contributions disclosed herein may be specifically pointed out below, whereas other such contributions encompassed by the present disclosure the invention will be apparent from their context.

Often when diagnosing mobile devices to detect faults in different components of the mobile devices, the same set of diagnostic tests is performed on each mobile device regardless of, for example, the model or make of the mobile device under diagnostics. While this type of brute-force approach may provide a sure-fire method for diagnosing each mobile device if said set of diagnostic tests comprises all the relevant diagnostic tests available, it is not the most expedient or time-efficient solution in most cases. The failure probability of a mobile device may depend on various device-specific factors such as the type, model and age of the mobile device. To further complicate the matter, some components of a mobile device may be more prone to breaking than others and are thus more likely to be faulty and in need for replacement or repair at any given time. This fault likelihood for each component may also be a device-specific property. Thus, for a given mobile device some diagnostic tests in the set of diagnostic tests to be performed may be considered of high importance for achieving a successful diagnosis while others may be considered redundant or at least excessive. If all or at least some of the aforementioned factors could be taken into account in performing diagnostic testing of a mobile device, a significant improvement in the time required for testing each mobile device could be achieved.

BRIEF DESCRIPTION

According to an aspect, there is provided the subject matter of the independent claims. Embodiments are defined in the dependent claims.

One or more examples of implementations are set forth in more detail in the accompanying drawings and the description below. Other features will be apparent from the description and drawings, and from the claims.

BRIEF DESCRIPTION OF THE DRAWINGS

In the following the invention will be described in greater detail by means of preferred embodiments with reference to the attached drawings, in which.

DETAILED DESCRIPTION OF SOME EMBODIMENTS

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
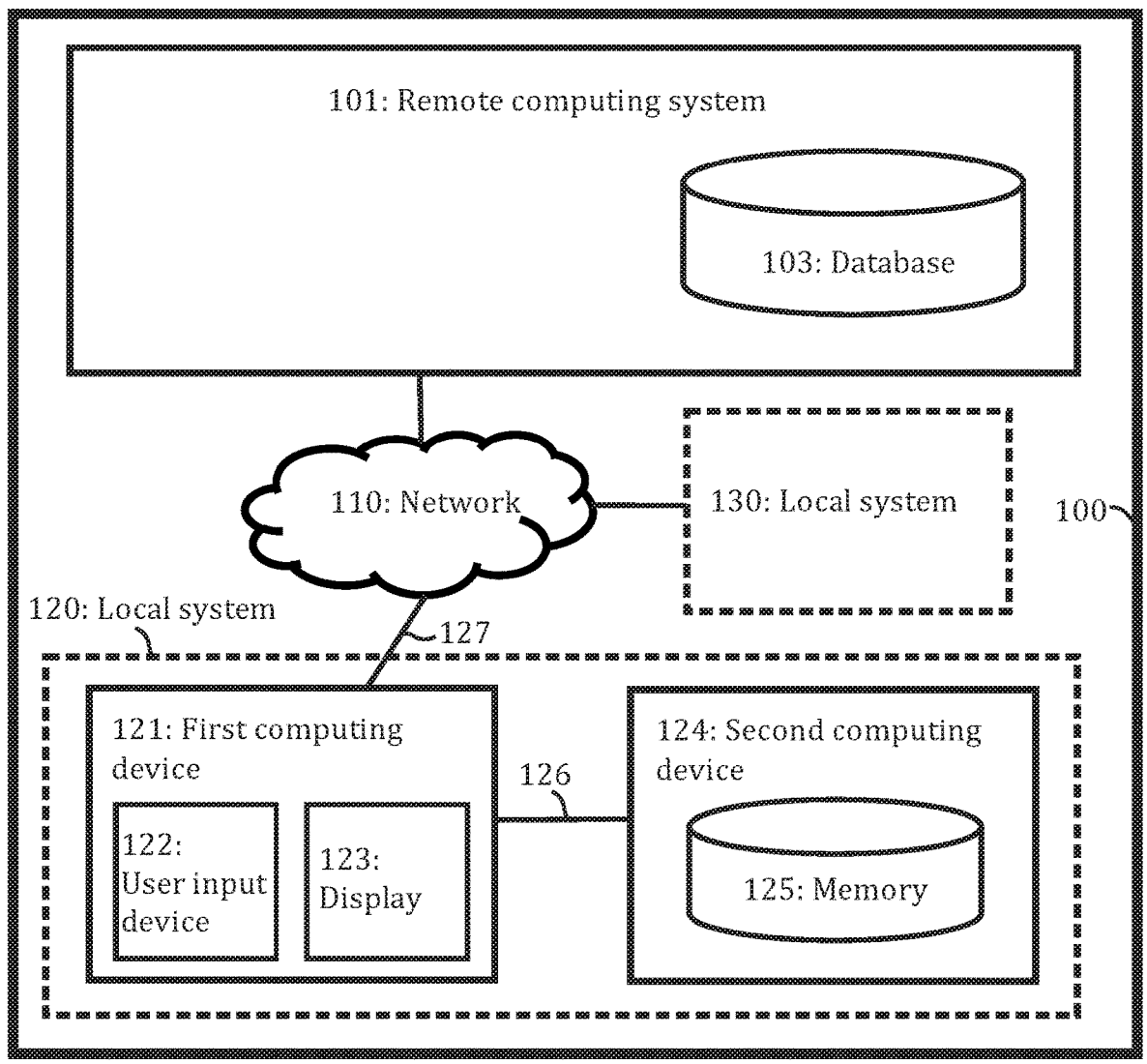
FIG. 1 illustrates a system according to embodiments.

An architecture of a communications system to which embodiments of the invention may be applied is illustrated in FIG. 1. FIG. 1 illustrates a simplified system architecture only showing some elements and functional entities, all being logical units whose implementation may differ from what is shown. The connections shown in FIG. 1 are logical connections; the actual physical connections may be different. It is apparent to a person skilled in the art that the systems also comprise other functions and structures.

FIG. 1 illustrates a system 100 comprising a remote computing system 101 which is connected via a communications network 110 to one or more local systems 120, 130. Each local system 120, 130 comprises at least a first computing device 121 connected via a first interface 126 to a second computing device 124 and via a second interface 127 to the communications network 110 (shown in FIG. 1 only for the local system 120 for simplicity). In some embodiments, the first computing device 121 in at least some of the one or more local systems 120, 130 may be connected via first interfaces 126 to two or more second computing devices 124 simultaneously.

The first computing device 121 is a computing device capable of performing or causing performing of a plurality of diagnostic tests on the second computing device 124 in a controlled manner. To be able to perform said diagnostic tests or cause them to be performed by the second computing device 124 itself, the first computing device 121 may be configured, for example, to access information (e.g., device information and/or results of one or more diagnostic tests) stored to the second computing device 124, send information (e.g., device parameters or a generated diagnostic report) to the remote computing system 101 via the communications network 110 using the second interface 127, receive information (e.g., predicted results of one or more diagnostic tests when performed on the second computing device or lack thereof and/or other diagnostics information) from the remote computing system 101 via the communications network 110 using the second interface 127 and running one or more diagnostic tests on the second computing device 124. The running of the one or more diagnostic tests on the second computing device 124 may specifically comprise instructing or commanding the second computing device 124 to execute the one or more diagnostic tests and to transmit results of the one or more diagnostic tests back to the first computing device 124 or executing the one or more diagnostic tests targeting the second computing device 124 using the first computing device 121 (with the second computing device 124 having a predominantly passive role in running the one or more diagnostic test). A combination of these two options is also possible, in some embodiments. Moreover, the first computing device 121 may comprise at least one user input device 122 which provides a user of the first computing device 121 means for inputting information, for example, in connection with the diagnostic testing. The at least one user input device 122 may comprise, for example, a keyboard, a touch screen, a mouse, a touch pad and/or voice activated control device. The first computing device 121 further comprises a display 123 through which the user may be able to monitor the running of the diagnostic tests. The first interface 126 may be used, by the first computing device 121, at least for retrieving device information and/or results of one or more diagnostic tests from the second computing device 124 (or specifically from the memory 125 thereof) when performing the diagnostic test(s). The first computing device 121 may be connected via the first interface 126 to the second computing device 124 using a wire or a cable such as a USB (Universal Serial Bus)-to-USB cable, a USB-to-mini-USB cable or a USB-to-micro-USB cable, using a docking station or wirelessly (e.g., via WiFi or Bluetooth). The first computing device 121 may be configured to run dedicated diagnosis client software for guiding a user or an operator of the first computing device 121 through the diagnosing of the second computing device 124.

The second computing device 124 is a computing device which is to be diagnosed using the first computing device 121. The second computing device 124 may comprise one or more memories. While the first computing device 121 may be actively operated by a user or an operator, the second computing device 124 may be configured only (or at least for the most part) to receive user inputs via the to first computing device 121 (that is, not via any possible user input devices of the second computing devices 124) during the processes according to some embodiments to be discussed in the following. In some embodiments, some of the diagnostic tests may require input from the user directly via a user input device of the second computing device 124 (e.g., testing operation of a push-button, a touch sensor, a fingerprint sensor, a speaker or a screen).

Each of the first and the second computing device 121, 124 refer to a portable or non-portable computing device (equipment, apparatus). Computing devices which may be employed include wireless mobile communication devices operating with or without a subscriber identification module (SIM) in hardware or in software, including, but not limited to, the following types of devices: desktop computer, laptop, touch screen computer, mobile phone, smartphone, personal digital assistant (PDA), handset, e-reading device, tablet, game console, note-book, multimedia device, sensor, actuator, video camera, car, wearable computer, telemetry appliances, and telemonitoring appliances. The first and second computing devices 121, 124 may be computing device of the same type or of a different type. In a typical non-limiting embodiment, the first computing device 121 may be a desktop computer or a laptop and the second computing device 124 may be a mobile device (e.g., a smartphone, a tablet computer or a laptop). In general, the second computing device 124 may be any computing device which may be electrically connected to the first computing device 121.

The second computing device 124 may comprise a plurality of different components (or parts) operation of which may be diagnosed. For example, said plurality of components may comprise one or more components of one or more of the following types or categories: a touch sensor, a speaker, a screen, a connector, a proximity sensor, a microphone, a light (e.g., a LED light), a heartbeat monitor, a headphone jack, a headset, a front camera, a back camera, a push-button, a fingerprint sensor, a near-field communication (NFC) component, a receiving speaker, a battery, a temperature sensor, a barometer, a vibrator motor, a compass, a camera flash, an autofocus, an auto rotation sensor and an infrared sensor. The plurality of components may comprise one or more components of the same type. Each diagnostic test may diagnose operation of a single component or multiple components of the same and/or different category simultaneously.

In some embodiments, the first computing device 121 and the second computing device 124 may be parts of a single apparatus or the second computing to device 124 may be comprised within the first computing device 121. In other words, the first and second computing devices may be fixed together (as opposed to being easily detachable from each other as discussed earlier). For example, the second computing device 124 may correspond to a memory or a storage device of the first computing device 121.

The communications network 110 may comprise one or more wireless networks, wherein a wireless network may be based on any mobile system, such as GSM, GPRS, LTE, 4G, 5G and beyond, and a wireless local area network, such as Wi-Fi. Furthermore, the communications network 110 may comprise one or more fixed networks and/or the Internet.

The remote computing system 101 is a device configured to receive information (e.g., device information, such as one or more device parameters, characterizing the computing device) regarding second computing devices 124 from first computing devices 121 connected to it via the communications network 110, analyze the received information and send analysis results (e.g., predicted diagnosis results and/or other diagnostic guidance information) to the first computing devices 121 via the communications network 110. The analysis may be carried out specifically by a diagnostic analysis unit or apparatus of the remote computing system (not shown in FIG. 1) and/or may be based on information stored to a diagnostic report database 103 connected to or comprised in the remote computing system. The diagnostic report database 103 may comprise at least a plurality of diagnostic reports describing results of diagnostic tests performed by first computing devices (i.e., by the first computing device 121 and/or other corresponding devices) on second computing devices (i.e., on the second computing device 124 and/or other corresponding devices), to be described in detail in relation to further embodiments.

The other diagnostic guidance information sent to the first computing devices 121 by the remote computing system 101 may comprise, for example, information on the second computing device 124 maintained in the diagnostic report database of the remote computing system 101. Such information may relate, for example, to errors or warnings given by the second computing device 124 (or specifically, by a dedicated user application running on the second computing device 124) during its operation. In addition to or alternatively, the other diagnostics information may comprise nominal or reference values indicated by the manufacturer of the second computing device and/or further statistical information on the diagnostic tests performed on the plurality of computing devices.

The remote computing system 101 may be equally called a remote server or a server as seen by the first computing device 121. In other words, the first computing device 121 and the remote computing system may be seen as forming a client-server relationship. Similarly, the first computing device 121 may be equally called a local client or a client.

According to an embodiment, the first computing device 121 is connected to multiple second computing devices 124 via USB (Universal Serial Bus) interface 126 using a USB hub. This embodiment provides the advantage that the number of USB ports in the first computing device may be fewer than the number of second computing devices handled by the first computing device. According to an embodiment, the USB hub is a 10-port USB hub.

The remote computing system 101 may be fully or partly cloud-based, that is, the remote computing system 101 may be or comprise at least one computing cloud. Specifically, the diagnostic analysis unit and/or the diagnostic report database may be cloud-based.

The embodiments to be discussed below seek to facilitate and/or expedite the process of diagnosing a computing device (e.g., the second computing device 124 of FIG. 1). The computing device to be diagnosed may specifically be a mobile (computing) device such as a smartphone or a tablet computer, though the embodiments are not limited to mobile devices. A conventional mobile device such as a smartphone or a tablet computer comprises a large number of components (e.g., a front and/or back camera, a screen and a touch sensor) which may become faulty during the lifetime of the mobile computing device. Different diagnostic tests may be performed on the mobile device to determine whether one or more components of the mobile computing device are working correctly. In order to fully diagnose a computing device, a large number of different diagnostic tests may have to be performed which may take a considerable amount of time. It would be advantageous if the amount of time required for the diagnosing a single mobile device could be reduced without considerably compromising the quality of the diagnosis (i.e., without causing component faults to be missed). The likelihood of a particular component becoming faulty differs depending at least on the type of the component and the age of the mobile device. For example, for a mobile device which is at least one year old, the probability that the screen is not working correctly may be relatively high while the probability that there is a problem with the microphone may be almost zero. Thus, in diagnosing the mobile device the performing of the to diagnostic test for diagnosing the status or condition of the screen should be prioritized over the performing of the diagnostic test for diagnosing the status or condition of the microphone. In other words, the diagnostic test for the microphone may be skipped with relative safety while the diagnostic test for the screen should probably not be skipped. However, while this principle may apply in most cases, the microphone in a mobile device of a particular model may be known to be considerably more likely to fail than most microphones and thus the diagnostic test for the microphone should be performed on that particular model. It would require a huge amount of effort from a user to keep track of all the various factors effecting the fault probabilities of each component of each device so as to make informed decisions regarding which diagnostic tests should be performed on a particular mobile device. The embodiments facilitate this decision-making by providing relevant statistical information regarding the mobile device and its fault probabilities.

Figure 2:
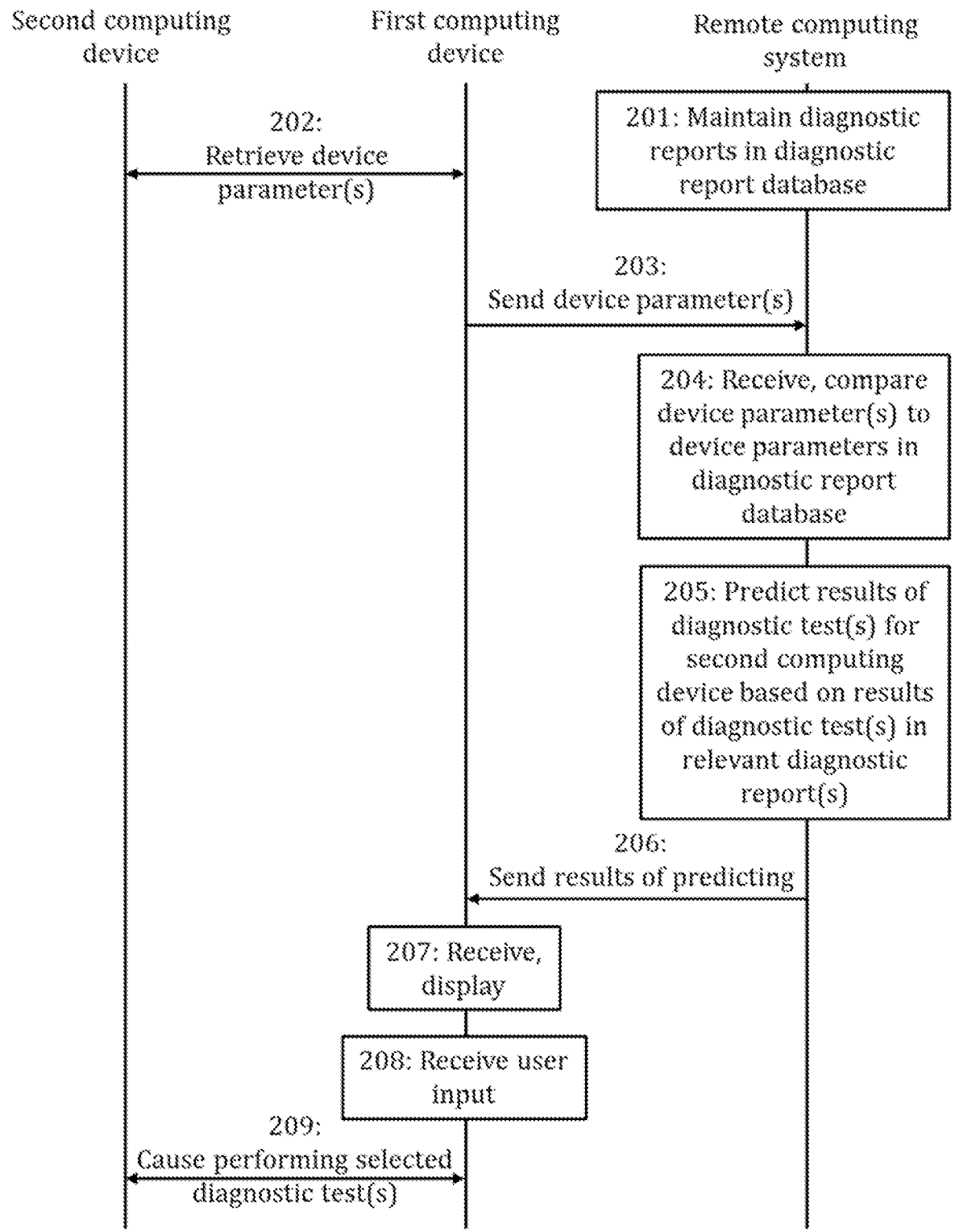
FIGS. 2 to 7 illustrate processes according to embodiments.

FIG. 2 illustrates signaling, according to embodiments for providing a user with information on predicted results for at least one diagnostic test to be performed on a second computing device and performing the diagnosing using a first computing device. The illustrated processes may be carried out using a system 101 of FIG. 1. While the illustrated process (and also the following illustrated processes) are discussed for a first computing device acting on a single second computing device, in other embodiments multiple second computing devices may be handled by the first computing device in a similar manner simultaneously (i.e., in parallel).

Referring to FIG. 2, it is initially assumed that the remote computing system maintains, in block 201, in a diagnostic report database a plurality of diagnostic reports on a plurality of computing devices. Each diagnostic report comprises results of one or more diagnostic tests performed on a computing device of the plurality of computing devices and a set of one or more device parameters characterizing said computing device. Said results of one or more diagnostic tests performed on a computing device of the plurality of computing devices may comprise at least information on one or more diagnostic tests (or processes) performed on a particular computing device and on the outcome (or diagnosis) of each of said one or more diagnostic tests. The information on the outcome of a diagnostic test may at least indicate whether or not the diagnostic test gave a positive or negative diagnosis (i.e., indicated correct operation or a failure of the relevant component or components of the computing device). In some embodiments, the information on to the outcome of a diagnostic test may also provide further information on the detected failure (e.g., in the form of an error code) and/or a duration of the diagnostic test. One or more diagnostic reports may be maintained for each of the plurality of computing devices. The set of one or more device parameters for a given computing device may comprise, for example, one or more of a manufacturer, a model, a year or date of manufacture, International Mobile Equipment Identity (IMEI) or other a device identifier, hardware information (e.g., component information), type and/or capacity of at least one memory, operating system, at least a part of a log history of the computing device and/or the age of the computing device. A more comprehensive list of possible device parameters is provided after the discussion on FIG. 2.

The process for guiding a user in selecting diagnostic test(s) for diagnosing a second computing device starts when a first computing device retrieves, in messages 202, a first set of one or more device parameters characterizing the second computing device electrically connected to the first computing device from a memory of the second computing device. The retrieving in messages 202 may be initiated in response to establishing a connection between the first and second computing devices (e.g., in response to connecting the two devices with a USB cable or some other cable). According to an embodiment, in addition to retrieving one or more device parameters from a memory of the second computing device, the first computing device also retrieves one or more further device parameters from a remote computing system, where these parameters are maintained in a database. According to an embodiment, said further device parameters are maintained in the same remote computing system where diagnostic reports are maintained in the diagnostic report database.

The one or more device parameters in the first set may be defined as described above in relation to the contents of a diagnostic report. The retrieving may specifically comprise sending, by the first computing device, a request for device parameters to the second computing device and in response to receiving the request in the second computing device, retrieving, by the second computing device, the first set of one or more device parameters from a memory of the second computing device and sending them from the second computing device to the first computing device. After the retrieving, in messages 202, the first computing device sends, in message 203, the first set of one or more device parameters (or at least a subset therein) characterizing the second computing device via a communications network to a remote computing system. The first set of one or more device parameters may be sent within a separate request for predicting results of one or more diagnostic tests for the second computing device or as a part of regular reporting operation of the first computing device. In some alternative embodiments, the second computing device may send one or more of its own device parameters (via the communications network) to the remote computing system. In some embodiments, the retrieving in block 202 may be initiated automatically in response to the second computing device being electrically connected to the first computing device.

In response to receiving, in block 204, a first set of one or more device parameters characterizing (or defining) the second computing device from the first computing device via the communications network, the remote computing system compares, in block 204, the first set of one or more device parameters to the plurality of sets of device parameters comprised in the plurality of diagnostic reports maintained in the diagnostic report database. Specifically, the remote computing system may compare the first set to each of the plurality of sets to find one or more diagnostic reports relevant for the second computing device. The diagnostic reports with matching device parameters are considered relevant (or applicable or pertinent) for the second computing device as they correspond to the same or similar computing devices as the second computing device. Thus, the comparing may comprise searching for matches for the one or more device parameters in the first set from the plurality of diagnostic reports, where the matches may be required to be full matches and/or close or partial matches (e.g., at least some device parameters given in a diagnostic report match the one or more device parameters in the first set or a full set of device parameters given in a diagnostic report is correlated with the first set of one or more device parameters to a certain degree). A different importance or weight may be applied for each device parameter in the comparing. For example, an acceptable partial match for a second computing device being a smartphone could be a smartphone of the same model and the same age within one year but having a processor of higher clock rate. In other words, larger weights may applied, in the comparing, for device parameters of a model of the computing device and the age of the computing device while a smaller weight may be applied to a device parameter of a processor clock rate. The comparing procedure according to an embodiment is to be described in more detail in connection with FIG. 3.

Based on the comparing in block 204 or more specifically on results of the one or more relevant diagnostic reports, the remote computing system predicts, in block 205, results of one or more diagnostic tests when performed on the to second computing device based on results of one or more diagnostic tests in the one or more relevant diagnostic reports by using statistical analysis. The predicting may comprise evaluating at least a predicted probability of a positive (i.e., favourable) diagnosis for each of the one or more diagnostic tests when performed on the second computing device (i.e., probability for each diagnostic test failing to indicate a fault, defect or breakage in corresponding component(s) of the second computing device). If the one or more relevant diagnostic reports comprise not only diagnostic reports relating to fully matching computing devices but also one or more computing devices matching the second computing device only partially, the extent of the mismatch may be taken into account in the predicting. For example, the fully or highly matching diagnostic reports may be weighted in the predicting relative to the moderately well matching diagnostic reports.

In general, the predicted results of one or more diagnostic tests when performed on the second computing device may comprise, for each diagnostic test, one or more statistical metrics derived from the results of the diagnostic tests. Said one or more statistical metrics may comprise, for example, said predicted probability of a positive diagnosis and one or more related uncertainty metrics (e.g., the number of diagnostic reports on which the prediction is based).

In some embodiments, the remote computing system predicts, in block 205, one or more components of the second computing device which are most likely to be defective based on the one or more relevant diagnostic reports. This prediction may be based on the aforementioned predicted probability of a positive diagnosis for one or more diagnostic tests as each diagnostic test may provide information regarding the functioning of a specific component or a specific group of components. The one or more components considered to be typically defective may be defined so as to comprise a pre-defined number of components or to comprise all components for which at least one diagnostic test is predicted to provide a positive diagnosis with a predicted probability which falls below a pre-defined threshold.

Modern mobile devices may comprise a group of components of the same type, such as multiple microphones and/or multiple loudspeakers, for example. According to an embodiment, a diagnostic test on loudspeakers provides information regarding the functioning of the whole group of loudspeakers or a subgroup therein. For example, the diagnostic test may provide information regarding the functioning of all loudspeakers, only those loudspeakers that produce audible sound or only those loudspeakers that function ("in reverse") as microphones. According to an embodiment, a diagnostic test provides information regarding the functioning of a specific loudspeaker. For example, the diagnostic test may provide information regarding the functioning of the front speaker designed to convert an electrical signal into an audible sound during a phone call.

Once the remote computing system has performed the predicting in block 205, it sends, in message 206, results of the predicting to the first computing device via the communications network for guiding a user of the first computing device in selecting suitable diagnostic tests for diagnosing the second computing device. The results of the predicting may comprise at least information on a predicted probability of a positive diagnosis for each of the one or more diagnostic tests when performed on the second computing device and/or information on one or more likely defective components of the second computing device. The results of the predicting may further comprise any of the information used for predicting the probabilities and information on how reliable each probability prediction is (e.g., how many diagnostic reports were considered relevant and were thus used for the prediction). In some embodiments, the results of the predicting sent to the first computing device may comprise a recommendation regarding whether a particular diagnostic test should be performed. Such a recommendation may be included in the information sent to the first computing device, for example, if a probability of a positive diagnosis for a diagnostic test is below a pre-defined threshold.

In some embodiments, a probability of a negative diagnosis (i.e., a failure rate) may be calculated (in block 205) and sent to the first computing device (in block 206), instead of a probability of a positive diagnosis (i.e., a success rate).

The first computing device receives, in block 207, at least the results of the predicting (and possibly other diagnostic guidance information) and subsequently (or consequently) displays, in block 207, said information to a user via a display of the first computing device. By providing the results of the predicting regarding one or more diagnostic tests to the first computing device and displaying them to the user of the first computing device, the decision making regarding which diagnostic tests (if any) to perform for diagnosing the second computing device using the first computing device is facilitated. Specifically, based on the displayed information the user may determine which diagnostic tests are unlikely to give a negative diagnosis taking into account various properties of the second computing device (i.e., device parameters) and may thus be skipped with relative safety if time for performing the diagnostics is limited.

In response to receiving a user input confirming a selection of one or more diagnostic tests via a user input device of the first computing device, the first computing device causes, in messages 209, performing of the one or more selected diagnostic tests for diagnosing the second computing device.

In some embodiments, the one or more selected diagnostic tests (or at least one of them) may be performed, in messages 209, as follows. The first computing device, first, generates a diagnostic test program (or simply instructions) for performing at least one diagnostic test by the second computing device and reporting results of said at least one diagnostic test back to the first computing device. Then, the first computing device sends said diagnostic test program to the second computing device. No particular diagnostics software needs to be pre-installed in the second computing device. In response to receiving said diagnostic test program, the second computing device executes the diagnostic test program. The execution of the diagnostic test program may be fully automatic or it may require user input via a user input device (e.g., a touchscreen, a push-button or an acceleration sensor) of the second computing device at one or more stages. For example, if the diagnostic test program pertains to diagnosing a speaker, the second computing device may prompt the user to confirm that a reference sound is heard when said sound is played. To give another example, diagnosing a push-button of the second computing device (e.g., a Home key) may require the user to push said push-button. The diagnostic test program instructs the second computing device to transmit the results of the at least one diagnostic test defined by the diagnostic test program to the first computing device. According to the diagnostic test program, the results may be sent automatically after the completion of said at least one diagnostic test. Alternatively, the user may be, first, prompted by the second computing device to approve the sending and the results may be sent only in response to the user providing their approval via a user input device of the second computing device. In some embodiments, a separate diagnostic test program may be generated for each diagnostic test while in other embodiments all of the one or more selected diagnostic test may be covered by a single diagnostic test program.

In some alternative embodiments, the selecting of one or more diagnostic tests and performing said one or more diagnostic tests may be performed automatically based on information received in block 207 (e.g., on success rates of different diagnostic tests). In such embodiments, at least block 208 is, thus, omitted.

The processes according to embodiments provide the advantage that since device-specific information on predicted results of one or more diagnostic tests (and possibly other diagnostic guidance information) are provided to the user of the first computing device, the user of the first computing device is capable of making more informed and expedient decisions regarding the selection of the diagnostic tests since the decision on the diagnostic test selection does not depend solely on the expertise of the user. If no device-specific information on predicted results of one or more diagnostic tests would be available for the user of the first computing device, the user would likely have to perform each available diagnostic test for the second computing device in order not to risk missing a fault in any component of the second computing device due to skipping the performing of a vitally important diagnostic test. In other words, the embodiments enable time-saving in performing diagnostic testing in a way which minimizes the chances for a missed negative diagnosis.

In some embodiments, the one or more device parameters retrieved by the first computing device and/or comprised in each diagnostic report may comprise one or more of the following hardware-related pieces of information regarding the device in question: a name of the manufacturer, a name, a model, a year or date of manufacture, an identifier for the device, IMEI, a serial number, an internal model, a chassis type, a rooting (e.g., rooted/not rooted), a (clock) speed of the processor of the computing device, a manufacturer of the processor of the computing device, a model of the processor of the computing device, information on at least some of one or more memories of the computing device and at least a part of a log history of the computing device.

The information regarding the chassis type of the computing device included in the one or more device parameters may comprise, for example, information on a form factor of the chassis, a material of the chassis and/or a manufacturer of the chassis. According to an embodiment, the information regarding the chassis type indicates whether the chassis is made partially or wholly of plastic or metal. According to an embodiment, the information regarding the chassis type indicates whether the chassis is reinforced with an extra cover, protective layer, coating or surface treatment.

The information on at least some of one or more memories of the computing device may comprise, for example, a name for each or some of one or more memories of the device, capacity for each or some of said one or more memories (given, e.g., in megabytes), type of each or some of said one or more memories, a serial number for each or some of said one or more memories, a vendor for each or some of said one or more memories and/or condition monitoring information from said one or more memories. According to an embodiment, the condition monitoring information may comprise indicators detected by the in-built S.M.A.R.T. (SelfMonitoring, Analysis and Reporting Technology) system of a hard disk drive (HDDs), solid-state drive (SSDs) or embedded Multi-Media Controller (eMMC) drive of the computing device. According to an embodiment, the condition monitoring information may comprise information on the number or percentage of bad memory units (blocks or sectors) in said one or more memories.

In some embodiments, the one or more device parameters retrieved by the first computing device and/or comprised in each diagnostic report may further comprise one or more of the following software-related pieces of information regarding the device in question: a name of the operating system, a version of the operating system, a software used for performing the diagnostic test(s), a version of said software used for performing the diagnostic test(s) and a source or vendor of said software used for performing the diagnostic test(s).

In some embodiments, the one or more device parameters retrieved by the first computing device and/or comprised in each diagnostic report may comprise the age of the computing device and/or the effective age of the computing device (evaluated, for example, based on the at least a part of the log history of the computing device or capacity deterioration of a battery of the computing device). Obviously, an almost new smartphone (or other computing device) is much less unlikely to be faulty than a three-year-old identical smartphone. Therefore, the (effective) age of the computing device may be a very significant factor in determining the one or more relevant diagnostic report (in block 204) and in predicting the results of the one or more diagnostic tests (in block 205). In general, the effective age may be defined as a metric quantifying the amount of deterioration in the performance of the computing device (compared to optimal performance of a new computing device). The effective age may be indicative of how heavily said computing device has been used during its lifetime. The age and/or effective age may be given in years, months or days and possibly as a non-negative integer.

The one or more device parameters retrieved by the first computing device and/or comprised in each diagnostic report may, also or alternatively, comprise information on use history of the computing device. According to an embodiment, the information on use history of the computing device is comprised in the at least a part of the log history of the computing device. For example, the use history may reveal how actively and for what types of tasks the computing device has been used. This information may be important as a smartphone used solely for occasional phone calls is likely to be less prone to breakage compared to a smartphone used extensively for a variety of demanding tasks such as playing music, video chats, setting up a mobile access point and augmented reality-based gaming. Such a difference in usage history would likely be visible also as a difference in the effective ages of the computing devices.

According to an embodiment, said at least a part of the log history is at least a part of a memory log, a log of applications installed on the computing device, a battery charging log and/or a battery temperature log. According to an embodiment, the memory log comprises information on the number or percentage of bad memory units (blocks or sectors) in one or more memories of the computing device. According to an embodiment, the battery charging log comprises information on how many times the battery of the mobile device has been charged and/or discharged. According to an embodiment, the battery temperature log comprises information on the maximum and the minimum temperatures the battery has been exposed to and the duration of the exposure.

Figure 3:
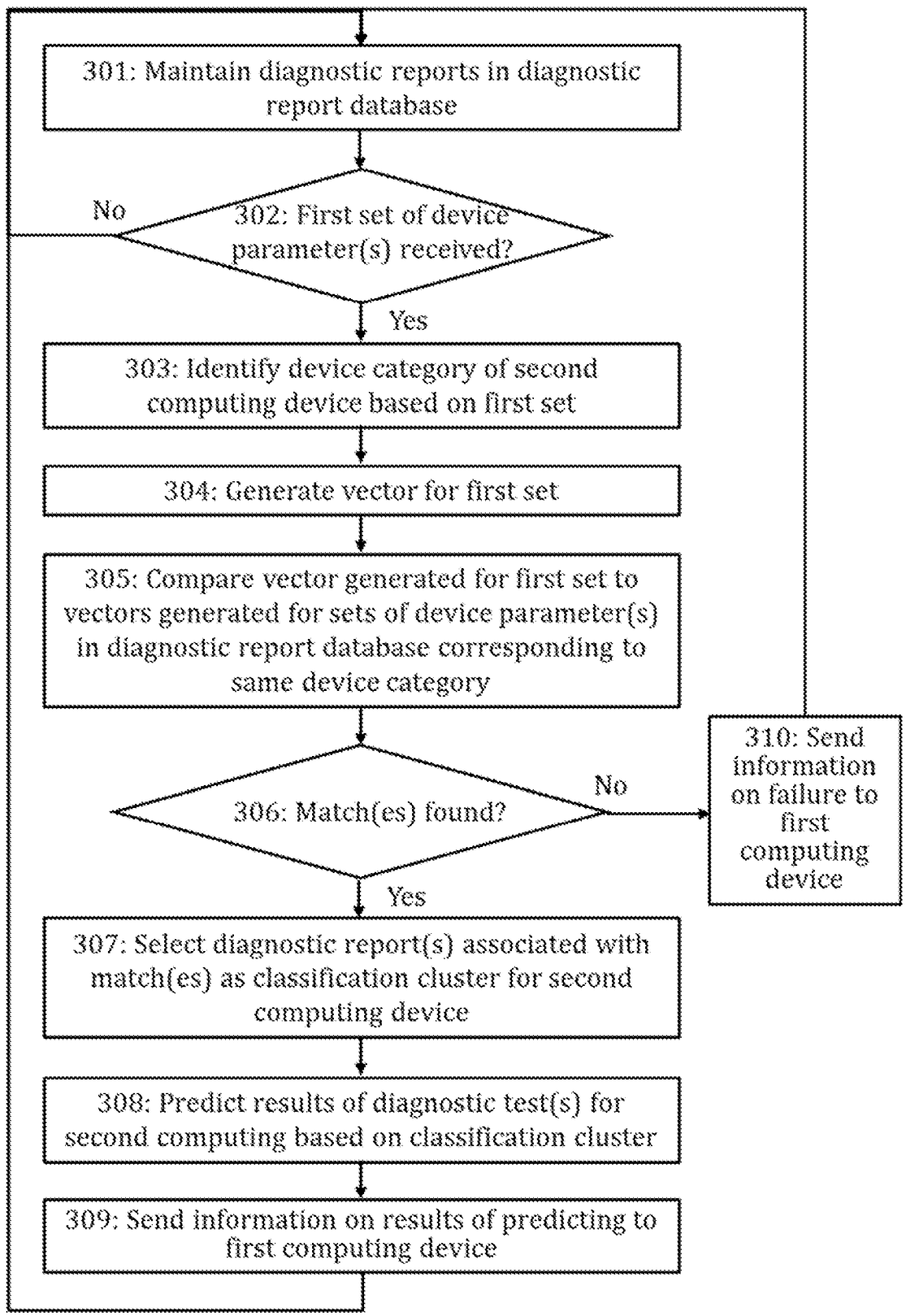

FIG. 3 illustrates a process performed by a remote computing system according to an embodiment for providing a user with information on predicted results of one or more diagnostic tests for a second computing device. The illustrated process is an alternative to the process carried out by the remote computing system in blocks 201, 204, 205 and message 206 of FIG. 2. The illustrated process may be carried out by the remote computing system 101 of FIG. 1. Unless otherwise stated, the definitions given in relation previous embodiments may apply also here.

Similar to FIG. 2, it is initially assumed in block 301 that the remote computing system maintains a plurality of diagnostic reports in a diagnostic report database. The remote computing system receives, in block 302, information on a first set of one or more device parameters characterizing a second computing device from a first computing device via a communications network. Blocks 301, 302 may correspond to blocks 201, 204 ("receive" only) of FIG. 2.

In the embodiment illustrated in FIG. 3, the comparing described in relation to block 204 of FIG. 2 is divided into blocks 303 to 307. In a pre-processing phase, the remote computing system identifies, in block 303, a device category of the second computing device based on the one or more device parameters received from the first computing device. The device category may be one of the device parameters or it may be identified based on the one or more device parameters. The available device categories may comprise, for example, a mobile phone (or a smartphone), a tablet computer, a desktop computer, a laptop, a mass media storage, a smart watch, a digital still camera, a digital video camera, a mobile Internet device, a personal digital assistant (PDA), a handheld game console, a calculator and a personal navigation device or any subset of said categories. In one embodiment, the available device categories are a mobile device, a desktop computer and a laptop.

In some embodiments, the device categories may be defined in a more limited manner. For example, the device categories may be specific to a certain manufacturer, that is, a Samsung smartphone and Apple smartphone may be defined to be different device categories. Similar limitation based on some other device parameter (e.g., memory type or operating system) may be applied in other embodiments.

The remote computing system generates, in block 304, a vector based on at least one of the one or more device parameters in the first set and the identified device category. Specifically, a particular subset of one or more device parameters from the first set are selected as element(s) of the vector based on the identified device category. Each element of each vector may have a numerical value corresponding (or mapping) to a particular feature or features of the second computing device. Said at least one of the one or more device parameters based on which the vector is generated may comprise only device parameters which are considered relevant or significant for diagnosing the second computing device belonging to the identified device category. Each element of a vector may correspond directly to a device parameter or it may be generated based on one or more device parameters (e.g., if the device parameter does not have a numeric value and/or if multiple device parameters are used for generating the element).

To give a simplistic example, the vector for a smartphone may comprise three values describing manufacturer, model and capacity of memory. If the second computing device is, for example, Apple iPhone 8 with 64 GB of memory, the vector generated for the second computing device may be [1 1 1]. In other words, "Apple" may map to a numerical value of one for the first element of the vector, "iPhone 8" may map to a numerical value of one for the second element of the vector and "64 GB" may map to a numeric value of one for the third element of the vector. In this system, the vector

[1 1 2] may correspond, for example, to Apple iPhone 8 128 GB and the vector [1 2 2] may correspond, for example, to Apple iPhone 9 128 GB.

The remote computing system compares, in block 305, the vector associated with the second computing device to one or more corresponding vectors which were generated for one or more computing devices of the plurality of computing devices based on one or more sets of one or more device parameters in the plurality of diagnostic reports. Here, said one or more computing devices may be specifically computing devices of the same device category as the second computing device. The one or more corresponding vectors may be generated after (or simultaneously with) the generation of the vector for the second computing device. Alternatively, each of the one or more corresponding vectors may have been generated earlier (i.e., before the performing of the process of FIG. 3), for example, when a diagnostic report on that particular computing device was received by the remote computing system. The generated vectors may be maintained in the diagnostic report database.

In some embodiments, the comparing in block 305 may specifically comprise calculating, for the vector of the second computing device, a value of a distance metric quantifying the difference (or distance) between the vector of the second computing device and corresponding one or more vectors of other computing devices (of the same device category). The distance metric may be the Euclidean distance d which may be calculated using the equation $$d = \sqrt{\sum_{i=1}^{n} (q_i - p_i)^2},$$

where i is the index, n is the number of elements in each vector, $q=[q_1\ q_2\ \ldots\ q_n]$ is the vector of one of the one or more computing devices associated with the plurality of diagnostic reports and $p=[p_1\ p_2\ \ldots\ p_n]$ is the vector of the second computing device. Instead of the Euclidean distance, the difference between two vectors may be quantified using another (distance) metric. For example, a weighted Euclidean distance may be employed. The weighted Euclidean distance $d_w$ may be defined using the equation $$d_w = \sqrt{\sum_{i=1}^{n} w_i (q_i - p_i)^2},$$

where $w_i$ are weighting factors which may be defined independently for each vector element (i.e., for each index i). Referring to the above example with a threes element vector, the manufacturer (i.e., the first element) may, for example, have the largest weighting factor and the capacity of the memory (i.e., the third element) may have the smallest weighting factor. In some other embodiments, standardized Euclidean distance may be employed as the distance metric.

In some embodiments, the vector generation in block 304 may not depend on the identified device category, but the comparing in block 305 may so that said comparing is carried out only for one or more computing devices of the identified device category.

Based on the comparing in block 305, the remote computing system determines, in block 306, whether one or more of the one or more vectors associated with the same device category as the second computing device match the vector of the second computing device according to pre-defined criteria. Specifically, the pre-defined criteria may define that a value of the distance metric between the vector of the second computing device and the matching vector should be below a predefined (upper) threshold.

If no matches are found in block 306, the remote computing system may send, in block 310, information on the failure to predict results of any diagnostic tests to the first computing device via the communications network. In some embodiments, block 310 may be omitted.

If one or more matches according to pre-defined criteria is found in block 306, the remote computing system selects, in block 307, one or more diagnostic reports associated with said one or more matching vectors (matching the vector of the second computing device) as a classification cluster for the second computing device. In some embodiments, the classification cluster may be defined separately for each diagnostic test. The classification cluster represents a set of diagnostic reports whose relevant device parameters match the corresponding device parameters of the second computing device to a sufficiently high degree. The classification cluster(s) may correspond to the one or more relevant diagnostic reports as discussed in relation to block 204 of FIG. 2.

The remote computing system predicts, in block 308, results of one or more diagnostic tests for the second computing device based on the one or more diagnostic reports in the classification cluster by using statistical analysis. The predicting may be performed similar to as described in relation to FIG. 2 with the difference that, in this case, the predicting in block 308 is limited to the classification cluster and may be based on, alternative or in addition to the diagnostic information comprised in each relevant diagnostic report, to vectors associated with the classification cluster.

Also similar to the embodiment of FIG. 2, once the remote computing system has performed the predicting of the results of one or more diagnostic tests to for the second computing device in block 308, it sends, in message 309, information on the results of the predicting (e.g., the probabilities for a negative or positive diagnosis for each diagnostic test and/or information on one or more components most likely to be defective) to the first computing device via the communications network.

In some embodiments, the pre-processing described in relation to block 303 (i.e., identifying the device category) may be omitted. Subsequent analysis in blocks 306 to 309 may, in those cases, be carried out irrespective of the device categories associated with the second computing device and the plurality of diagnostic reports. In other words, instead of analyzing only diagnostic reports corresponding to the same device category (e.g., a smartphone) as the second computing device, all of the plurality of diagnostic reports (and corresponding vectors) may be involved in blocks 306 to 309.

Figure 4:
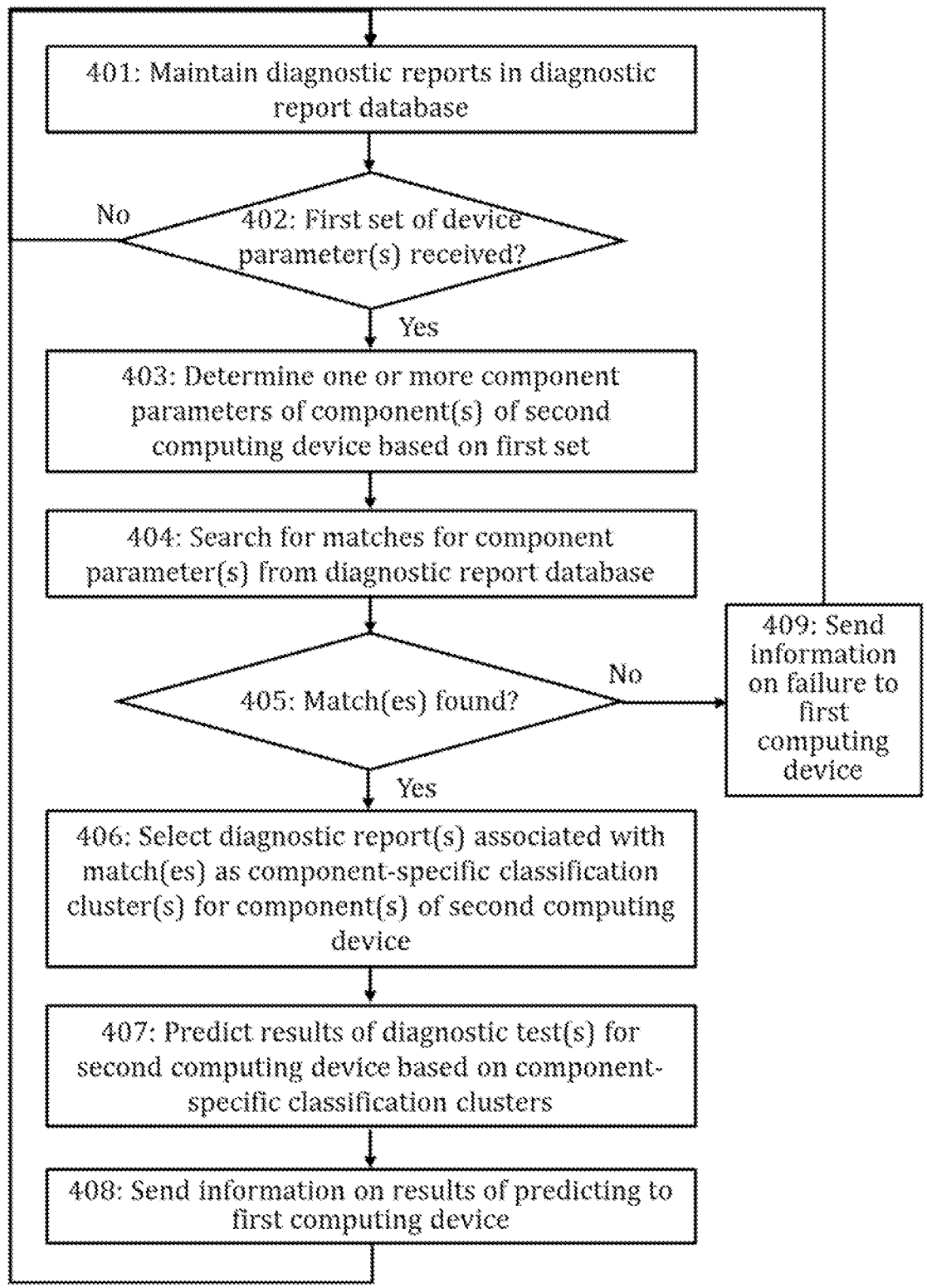

FIG. 4 illustrates another alternative process for providing a user with information on predicted results of one or more diagnostic tests for a second computing device. The illustrated process is an alternative to the process carried out by the remote computing system in blocks 201, 204, 205 and message 206 of FIG. 2 and to the process of FIG. 3. The illustrated process may be carried out by the remote computing system 101 of FIG. 1. Unless otherwise stated, the definitions given in relation previous embodiments may apply also here.

Referring to FIG. 4, the initial blocks 401, 402 may correspond to blocks 301, 302 of FIG. 3 and are thus not discussed here for brevity. In response to a first set of one or more device parameters having been received in block 402, the remote computing system determines, in block 403, for each of one or more components of the second computing device, a second set of one or more component-specific device parameters based on the first set of one or more device parameters received from the first computing device. Each second set may be a subset of the first set. The one or more component-specific device parameters in each second set may comprise, for example, a manufacturer of the component and/or a model of the component. Moreover, the one or more component-specific device parameters in each second set may comprise one or more component-specific device parameters which depend on the type of the component. For example, if the component in question is a front or back camera, the one or more component-specific device parameters in the corresponding second set may comprise resolution of the camera and/or support (or lack thereof) for Optical Image Stabilization (OIS) or simply a manufacturer of the camera. As another example, if the component in question is a mass media drive (e.g. HDD or SSD), the one or more component-specific device parameters may comprise support for a S.M.A.R.T. (Self-Monitoring, Analysis and Reporting Technology) monitoring system. Some device parameters (e.g., age and/or an effective age of the first computing device given in full years) may be included in all or most of the second sets of component-specific device parameters.

Then, the remote computing system searches, in block 404, for matches for one or more second sets of one or more component-specific device parameters from diagnostic report database. This search for a particular component defined through a second set of one or more component specific parameters may ignore all other features or properties of the computing device such as device category. Therefore, the matches for a second set of one or more component-specific device parameters (e.g., manufacturer and age) defining a back camera of a smartphone may comprise, for example, one or more diagnostic reports associated with smartphones with the same or similar back cameras and/or one or more diagnostic reports associated with tablet computers with the same or similar back cameras. The matches may be required to be full matches and/or close or partial matches. A different importance or weight may be applied for each device parameter in each second set.

If at least one match for at least one second set of one or more component-specific device parameters is found in block 405, the remote computing system selects, in block 406, for each second set of one or more component-specific device parameters for which at least one match was found, one or more diagnostic reports associated with the one or more corresponding matches as a component-specific classification cluster for said component. Subsequently, the remote computing system predicts, in block 407, the results of one or more diagnostic test(s) based on one or more component-specific classification clusters. Apart from the component-specific definition for the classification cluster, the predicting may be carried out as described in relation to block 309 of FIG. 3. Furthermore, actions pertaining to blocks 408, 409 may correspond to actions described in relation to blocks 309, 310 of FIG. 3.

Figure 5:
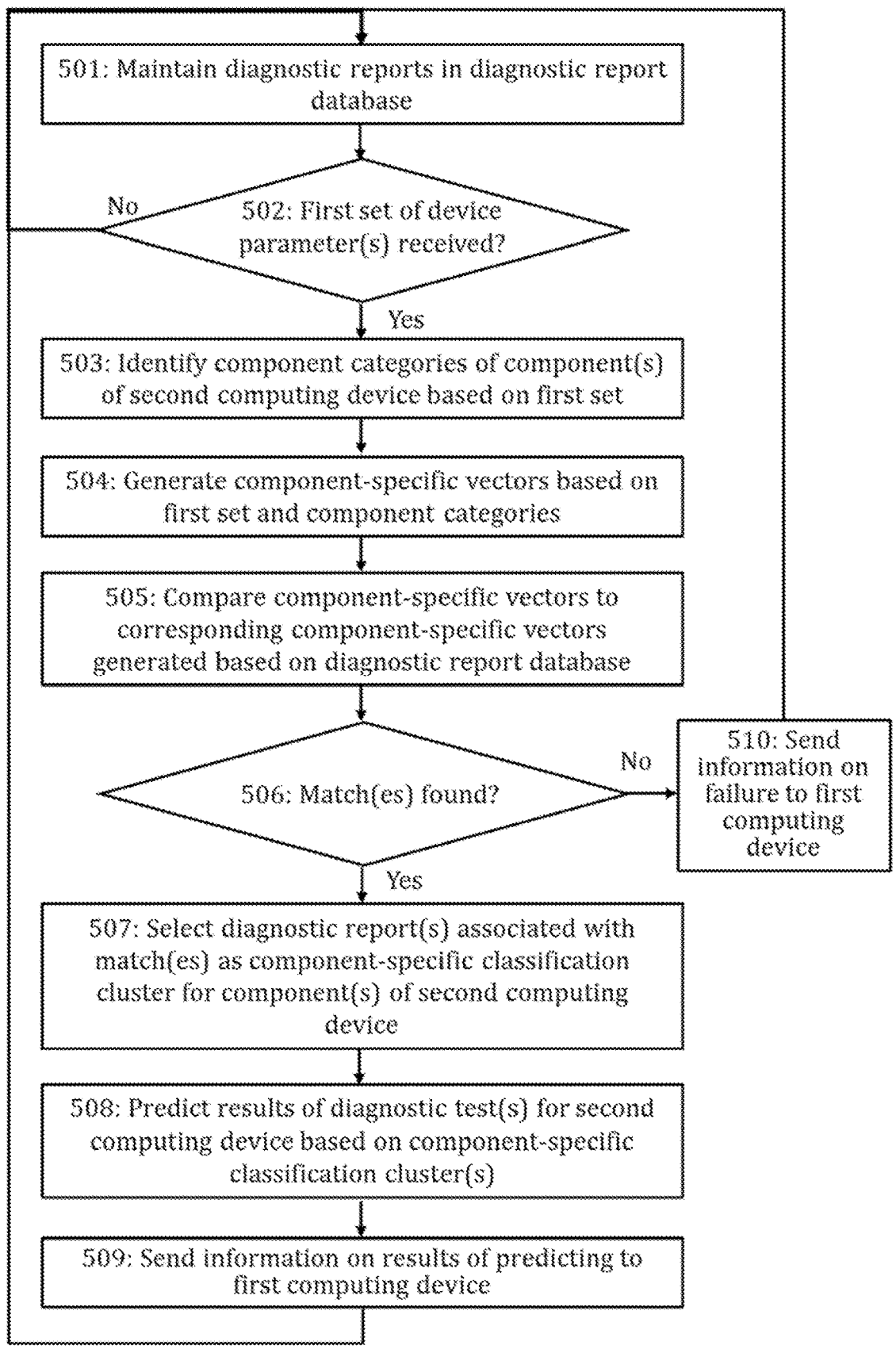

FIG. 5 illustrates another process for providing a user with information on predicted results of one or more diagnostic tests for a second computing device where the predicting is performed not only on a device level but on a component level, similar to FIG. 4. In contrast to FIG. 4, the process of FIG. 5 employs also the idea of generating vectors similar to FIG. 3. The process of FIG. 5 may, thus, be considered a combination of embodiments illustrated in FIGS. 3 and 4. The illustrated process is an alternative to the process carried out by the remote computing system in blocks 201, 204, 205 and message 206 of FIG. 2 and to the process of FIG. 3. The illustrated process may be carried out by the remote computing system 101 of FIG. 1. Unless otherwise stated, the definitions given in relation previous embodiments may apply also here.

Referring to FIG. 5, the initial blocks 501, 502 may correspond to blocks 301, 302 of FIG. 3 and are thus not discussed here for brevity. The basic idea of the process of FIG. 5 is to apply the process of FIG. 3 on a component level (as opposed to on a device level). Therefore, in response to a first set of one or more device parameters having been received in block 502, the remote computing system identifies, in block 503, a component category (e.g., a screen, a back camera or a touch sensor) of each of one or more components of the second computing device based on the first set of one or more device parameters. Thereafter, the remote computing system generates, in block 504, a component-specific vector for each of said one or more components based on the first set of one or more device parameters and the one or more identified component categories. Each element of each component-specific vector may have a numerical value corresponding (or mapping) to a particular feature or features of a particular component of the second computing device. Said at least one of the one or more device parameters based on which the component-specific vector is generated may comprise only device parameters which are considered relevant or significant for diagnosing that particular component of the second computing device. Each element of a component-specific vector may correspond directly to a device parameter or it may be generated based on one or more device parameters (e.g., if the device parameter does not have a numeric value and/or if multiple device parameters are used for generating the element). Some device parameters (e.g., age and/or effective of the second computing device) may be included in all or most of generated one or more component-specific vectors.

The remote computing system compares, in block 505, the one or more component-specific vectors of the second computing device to one or more corresponding component-specific vectors which were generated for one or more components of one or more computing devices of the plurality of computing devices based on one or more sets of one or more device parameters in the plurality of diagnostic reports. Said one or more corresponding component-specific vectors may have been generated previously (before the performing of the process of FIG. 5) and stored to the diagnostic report database. Alternatively, said one or more corresponding component-specific vectors may be generated between blocks 504 and 505 of FIG. 5 based on the plurality of diagnostic reports (or specifically, the drive parameters stored therein). The comparing may be carried out using a distance metric, similar to as described in relation to block 305 of FIG. 3 (though in this case the distance metric is defined for each component). Thus, in contrast to step 404 of FIG. 4, the component-specific comparing in block 505 may not only consider computing devices which are exact matches for one or more specific device parameters of the second computing device but also computing devices which are sufficiently similar (with regard to a particular component) to the second computing device.

Based on the comparing in block 505, the remote computing system determines, in block 506, whether one or more of the one or more component-specific vectors generated for the one or more computing devices match the one or more component-specific vectors of the second computing device according to predefined criteria. Similar to FIG. 3, the pre-defined criteria may define that a value of the distance metric between each component-specific vector of the second computing device and the matching component-specific vector should be below a predefined (upper) threshold. To give a practical example, this may mean, for example, that, in comparing vectors characterizing cameras of computing devices, not only back cameras having exactly the same specifications are considered matches but also any back cameras (or even any front or back cameras) with the same manufacturer (associated with a large weighting factor) and sufficiently similar specifications such as resolution (associated with smaller weighting factors).

If no matches for any component of the second computing device are found in block 506, the remote computing system may send, in block 510, information on the failure to predict results of any diagnostic tests to the first computing device via the communications network. In some embodiments, block 510 may be omitted.

If at least one match for at least one component of the second computing device is found in block 506, the remote computing system performs processes of blocks 507 to 509 which may correspond to blocks 406 to 408 of FIG. 4.

Figure 6:
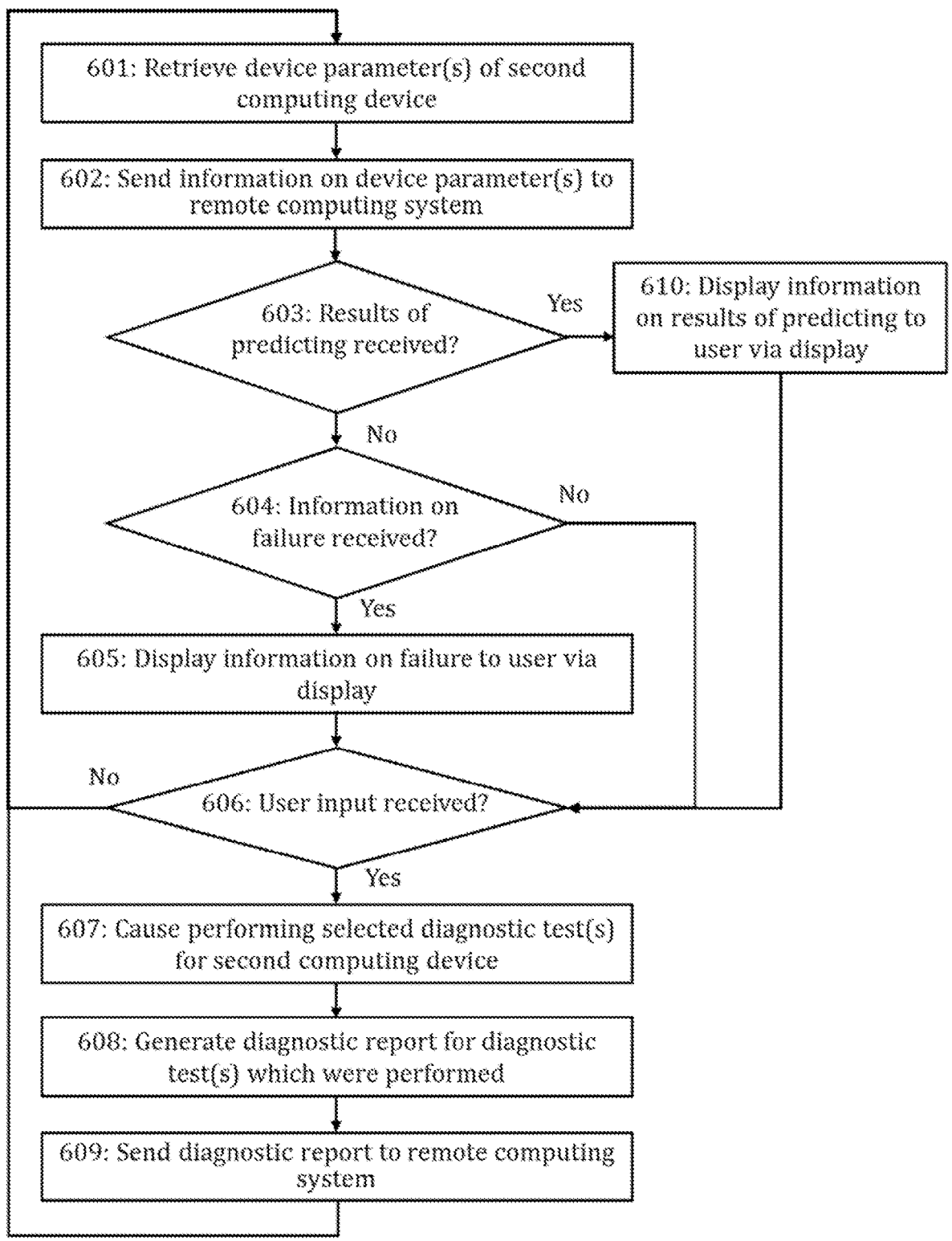

FIG. 6 illustrates a process performed by a first computing device according to an embodiment for diagnosing a second computing device electrically connected to the first computing device guided by information on predicted results of one or more diagnostic tests provided by a remote computing device. The illustrated process is an alternative to the process carried out by the first computing device in messages 202, 203, 209 and blocks 207, 208 of FIG. 2. The illustrated process may be carried out by the first computing device 121 of FIG. 1. Unless otherwise stated, the definitions given in relation previous embodiments may apply also here.

Referring to FIG. 6, the illustrated process corresponds in many aspects to the processes performed by the first computing device in FIG. 1. Actions pertaining to blocks 601, 602 may be carried out as described in relation to messages 202, 203 of FIG. 2. In response to receiving results of the predicting of one or more diagnostic tests (and possibly other diagnostic guidance information) for diagnosing the second computing device from the remote computing system via the communications network in block 603, the first computing device displays, in block 610, information on the received information to a user via a display of the first computing device. The received information (or at least some of it) may also be stored to a database connected to or comprised in the first computing device. The results of the predicting may be defined as described in relation to FIG. 2. In response to receiving information on a failure to predict results of any diagnostic tests in block 604, the first computing device displays, in block 605, information on the failure to the user via the display of the first computing device. If neither information is received in blocks 603, 604 (e.g., within a pre-defined time limit), the process may proceed directly to block 606 skipping block 605/610 (i.e., the displaying).

In response to receiving a user input confirming a selection of one or more diagnostic tests via a user input device of the first computing device in block 606, the first computing device causes, in block 607, performing of the selected diagnostic tests on the second computing device. Block 607 may be performed as described in relation to messages 209 of FIG. 2. The first computing device may also record (or store), in block 607, the results of each diagnostic test. In the ideal case, the user may make the selection regarding the diagnostic tests guided by predicted results (e.g., probability of a negative or positive diagnosis) for at least one diagnostic test. However, if no prediction results were received in block 603, the user may have to make the selection based purely on his/her own expertise. The user may also be allowed to make the selection of the diagnostic test(s) and initiate the diagnostic test(s) without having to wait for reception of any (possible) prediction results.

In response to the one or more selected diagnostic tests concluding, the to first computing device generates, in block 608, a diagnostic report on the one or more diagnostic tests which were performed on the second computing device. The diagnostic report may be defined as described above in relation to FIG. 2, that is, it may comprise at least the one or more device parameters of the second computing device and results of the one or more diagnostic tests. The results of each diagnostic test may comprise at least information on the outcome or diagnosis (i.e., the component is working correctly or the component has failed or is not working correctly) of the diagnostic test. The first computing device may include in the diagnostic report, in addition to the information on the outcome or diagnosis of the diagnostic test, one or more further diagnostic test properties such as the duration of the diagnostic test and/or at least some of the raw data generated by the diagnostic test.

In some alternative embodiments, the second computing device may generate the diagnostic report based on the one or more diagnostic tests which were performed on the second computing device, instead of the first computing device generating the diagnostic report, and subsequently send the generated diagnostic report to the first computing device.

Finally, the first computing device sends, in block 609, the generated diagnostic report to the remote computing system via the communications network. In some embodiments, the sending in block 609 may be performed only in response to receiving, via a user input device of the first computing device, a user input requesting the sending (or confirming the sending if the user was explicitly prompted to confirm the sending by the second computing device).

Figure 7:
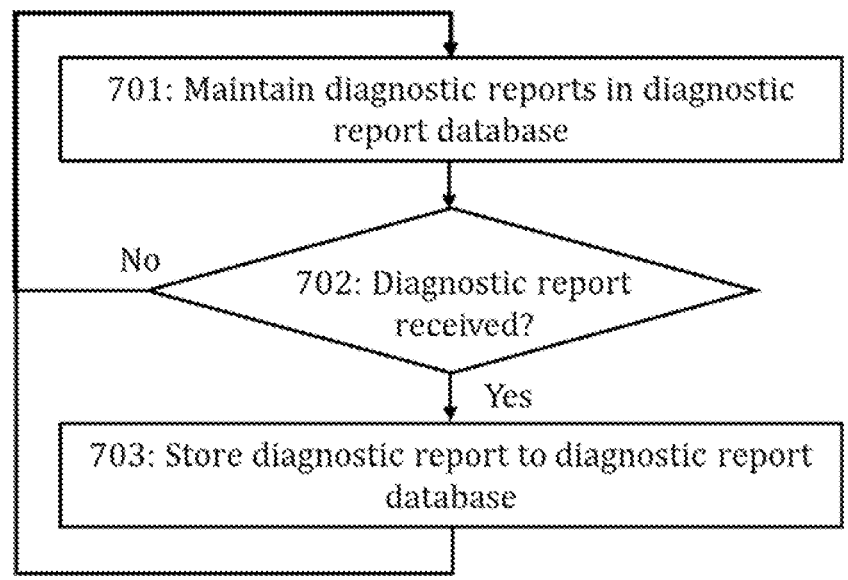

FIG. 7 illustrates a simple process for maintaining the diagnostic report database using the remote computing system. The remote computing system may be the remote computing system 101 of FIG. 1 and the diagnostic report database may the diagnostic report database 103 of FIG. 1. The illustrated process may be carried out in parallel with any of the processes of FIGS. 2 to 5 pertaining to the remote computing system or a part of said processes.

Similar to previous embodiments, it is initially assumed in block 701 the remote computing system maintains a plurality of diagnostic reports in a diagnostic report database. In response to receiving a diagnostic report on one or more diagnostic tests performed on a second computing device from a first computing device via a communications network in block 702, the remote computing system stores, in block 703, the received diagnostic report to the diagnostic report database. In some embodiments, the remote computing system may also send an acknowledgment acknowledging the successful reception of the diagnostic report to the first computing device via the communications network.

In some embodiments, the first computing device may be configured to perform any of the processes described in relation to FIGS. 2 to 7 simultaneously for multiple second computing devices electrically connected to the first computing device (that is, the same first computing device).

In the following, an exemplary use case for the embodiments from the point of view of an operator of a first computing device is discussed.

1. Raimo, the diagnostic technician, receives a batch of mobile phones which need to be diagnosed for estimating their potential for reuse potential. He sees that the shipment contains dozens of mobile phones with different models from various manufacturers.

2. Raimo takes the shipment next to his diagnostics work station (i.e., a first computing device) with a dedicated mobile device diagnosis application and having access to a cloud-based remote computing system.

3. Raimo starts to plug in (second computing) devices and sees how the devices show up in a user interface on a screen of the diagnostics work station. He sees that each of the connected devices go into preprocessing state.

4. After a short time, Raimo sees how the devices begin to receive the prediction data from the cloud-based remote computing system. He sees (at least) the predicted success rates for each diagnostic test in the user interface.

5. The estimates provided by cloud-based remote computing system look promising, except for one mobile phone. The metrics for that mobile phone show that the failure estimate for the display of the device is exceptionally high.

6. Raimo takes the phone under manual inspection and executes a diagnostic test for the display. Indeed, the display of the device is not fully functional. Therefore, he sets the device aside for further processing.

7. The rest of the batch looks promising, so Raimo selects randomly some devices and executes full diagnostics (i.e., a complete set of diagnostic tests) only for those.

8. Everything is fine with those devices, so Raimo is happy to proceed with the batch and moves it forward in the process.

Figure 8:
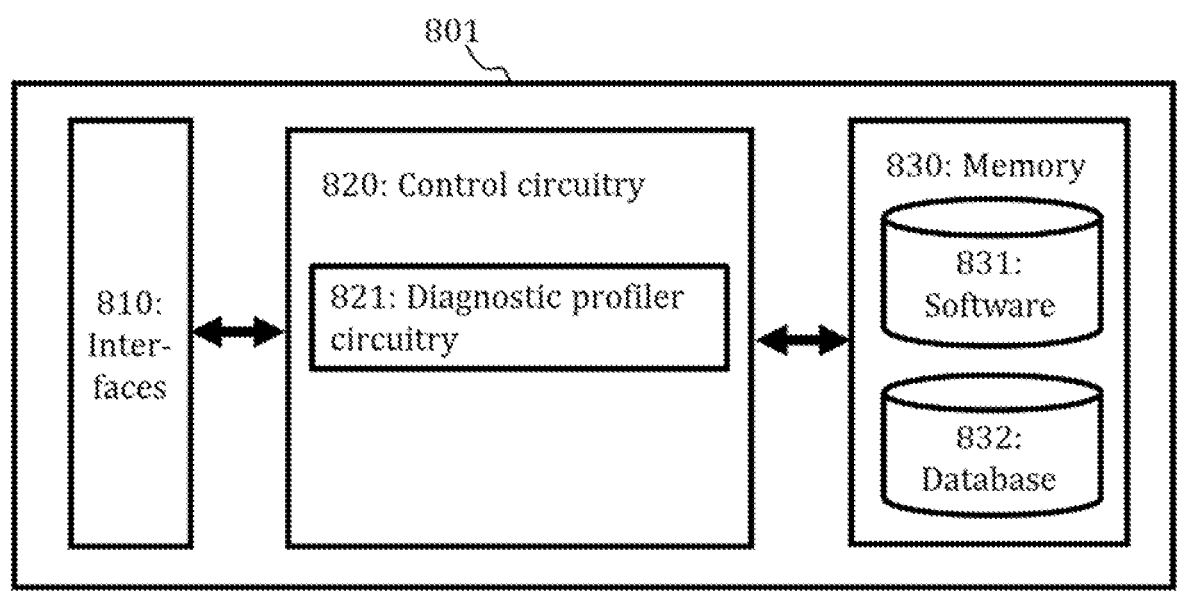
FIGS. 8 and 9 illustrate apparatuses according to embodiments.

FIG. 8 illustrates an apparatus 801 configured to perform the functions described above in connection with a remote computing system such as remote computing system 101 shown in FIG. 1. The apparatus may be an electronic device comprising electronic circuitries. The apparatus may be a separate network entity or a plurality of separate entities. The apparatus may comprise a control circuitry 820, such as at least one processor, and at least one memory 830 including a computer program code (software) 831 wherein the at least one memory and the computer program code (software) are configured, with the at least one processor, to cause the apparatus to perform any one of the embodiments of the remote computing system described above. The apparatus may comprise at least one database 832 which may comprise at least the diagnostic report database as described in relation to above embodiments.

The memory 830 may comprise a database 832 which may correspond to the diagnostic report database, as described in previous embodiments. The memory 830 may also comprise other databases which may or may not be related to the described diagnostic test prediction functionalities according to embodiments.

Referring to FIG. 8, the control circuitry 820 may comprise at least diagnostic profiler circuitry 821. The diagnostic profiler circuitry 821 may be configured, for example, to perform at least some of blocks 201, 204, 205 and message 206 of FIG. 2 and/or any of blocks in FIGS. 3 to 5 and 7.

Figure 9:
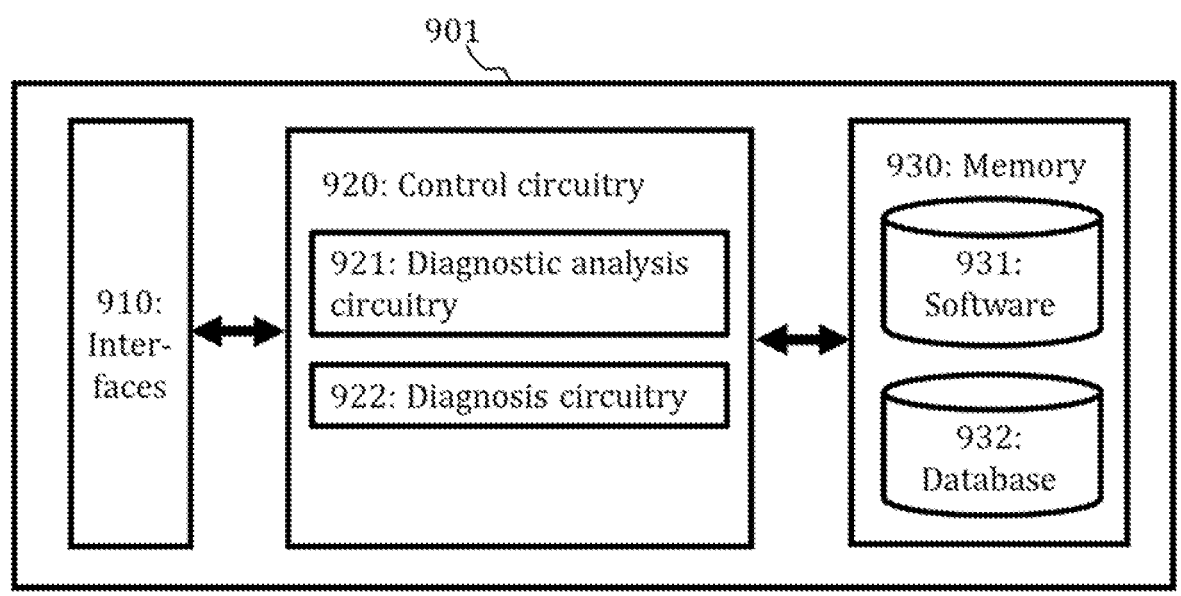

FIG. 9 illustrates an apparatus 901 configured to perform the functions described above in connection with a first computing device, such as the first computing device 121 of FIG. 1. The apparatus may be an electronic device comprising electronic circuitries. The apparatus may be a separate network entity or a plurality of separate entities. The apparatus may comprise a control circuitry 920 such as at least one processor, and at least one memory 930 including a computer program code (software) 931 wherein the at least one memory and the computer program code (software) are configured, with the at least one processor, to cause the apparatus to perform any one of the embodiments of the first computing device described above. The apparatus 901 may comprise, similar to the first computing device 121 of FIG. 1, a user input device and/or a display (not shown in FIG. 9).

The memory 930 may comprise a database 932 which may comprise, for example, information on one or more device parameters of one or more (second) computing devices electrically connected to the apparatus 901, prediction results received from a remote computing system via a communications network to and/or one or more diagnostic reports generated by the apparatus. The memory 930 may also comprise other databases which may or may not be related to the functionalities of the first computing device according to any of presented embodiments.

Referring to FIG. 9, the control circuitry 920 may comprise diagnostic analysis circuitry 921 configured to provide the first computing device functionalities for retrieving the device parameter(s) of the (second) computing device targeted for diagnosis and providing predicted diagnostic results regarding the second computing device to a user based on communication with a remote computing system and generating and sending to the remote computing system diagnostic reports according to any of presented embodiments. The control circuitry may further comprise diagnosis circuitry 922 configured to perform the selected diagnostic test(s). For example, the diagnostic analysis circuitry 921 may be configured to perform at least some of messages 202, 203 and/or blocks 207, 208 of FIG. 2 and/or any of blocks of FIG. 6 other than block 607. Moreover, the diagnosis circuitry 922 may be configured to perform at least messages 209 of FIG. 2 and/or block 607 of FIG. 6. In some other embodiments, the control circuitry 920 may be divided into three or more or only a single individual circuitry.

The apparatuses 801, 901 described in relation to FIGS. 8 and 9 may further comprise (communication) interfaces 810, 910 comprising hardware and/or software for realizing communication connectivity according to one or more communication protocols. The communication interface may provide the apparatuses with communication capabilities to communicate via a communications network and enable communication, for example, in the case of the apparatus 801 of FIG. 8 with one or more (first) computing devices and in the case of the apparatus 901 of FIG. 9 with a remote computing system. In the case of the apparatus 901 of FIG. 9, the communication interfaces 910 may provide a connection to one or more second computing devices, for example, using any means discussed in relation to FIG. 1.

The communication interfaces 810, 910 may comprise standard wells known components such as an amplifier, filter, frequency-converter, (de)modulator, and encoder/decoder circuitries and one or more antennas.

The memories 830, 930 of the apparatuses 801, 901 described in relation to FIGS. 8 and 9 may be implemented using any suitable data storage technology, such as semiconductor-based memory devices, flash memory, magnetic memory devices and systems, optical memory devices and systems, fixed memory and removable memory.

As used in this application, the term "circuitry" may refer to one or more or all of the following: (a) hardware-only circuit implementations (such as implementations in only analog and/or digital circuitry) and (b) combinations of hardware circuits and software, such as (as applicable): (i) a combination of analog and/or digital hardware circuit(s) with software/firmware and (ii) any portions of hardware processor(s) with software (including digital signal processor(s)), software, and memory(ies) that work together to cause an apparatus, such as a mobile phone or server, to perform various functions) and (c) hardware circuit(s) and or processor(s), such as a microprocessor(s) or a portion of a microprocessor(s), that requires software (e.g., firmware) for operation, but the software may not be present when it is not needed for operation.

This definition of circuitry applies to all uses of this term in this application, including in any claims. As a further example, as used in this application, the term circuitry also covers an implementation of merely a hardware circuit or processor (or multiple processors) or portion of a hardware circuit or processor and its (or their) accompanying software and/or firmware. The term circuitry also covers, for example and if applicable to the particular claim element, a baseband integrated circuit or processor integrated circuit for a mobile device or a similar integrated circuit in server, a cellular network device, or other computing or network device.

In an embodiment, at least some of the processes described in connection with FIGS. 2 to 7 may be carried out by an apparatus comprising corresponding means for performing at least some of the described processes. Some example means for performing the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, antenna, antenna circuitry, and circuitry. In an embodiment, the at least one processor, the memory, and the computer program code form (processing) means for or comprise one or more computer program code portions for performing one or more operations according to any one of the embodiments of FIGS. 2 to 7 or operations thereof.

Further regarding the means for performing the processes, the techniques and methods described herein may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chipset (procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with FIGS. 2 to 7 may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium. Coding of software for performing the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

It will be obvious to a person skilled in the art that, as the technology advances, the inventive concept can be implemented in various ways. The invention and its embodiments are not limited to the examples described above but may vary within the scope of the claims.

The invention claimed is:

1. A method comprising:
   maintaining, in a diagnostic report database, one or more diagnostic reports on each of a plurality of computing devices, wherein each diagnostic report comprises results of one or more diagnostic tests performed on a computing device of the plurality of computing devices and a set of one or more device parameters characterizing said computing device;
   receiving, by a remote computing system, a first set of one or more device parameters characterizing a second computing device via a communications network from a first computing device;
   comparing, by the remote computing system, in response to the receiving, the first set of one or more device parameters to a plurality of sets of device parameters in a plurality of diagnostic reports maintained in the diagnostic report database to find one or more diagnostic reports corresponding to the same or similar computing devices as the second computing device;
   predicting, by the remote computing system, results of one or more diagnostic tests when performed on the second computing device based on results of one or more diagnostic tests in the one or more diagnostic reports corresponding to the same or similar computing devices as the second computing device by using statistical analysis;
   sending, by the remote computing system, results of the predicting to the first computing device via the communications network;

selecting, based on the results of the predicting, one or more diagnostic tests for diagnosing the second computing device; and performing the one or more selected diagnostic tests on the second computing device.

2. The method of claim 1, wherein the results of the predicting comprise at least a predicted probability of a positive diagnosis given by each of the one or more diagnostic tests when performed on the second computing device and/or information on one or more components of the second computing device which are most likely to be defective.

3. The method according to claim 1, further comprising:
storing, by the remote computing system, in response to receiving by the remote computing system a diagnostic report for the second computing device from the first computing device, the diagnostic report to the diagnostic report database, wherein the diagnostic report comprises results of one or more diagnostic tests performed on the second computing device and the first set of one or more device parameters characterizing the second computing device.

4. The method according to claim 1, wherein the comparing of the first set of one or more device parameters to the plurality of sets of one or more device parameters further comprises:
generating, for the first set of one or more device parameters, a vector associated with the second computing device based on at least one device parameter in the first set, wherein each element of the vector associated with the second computing device has a numerical value representing a particular feature of the second computing device defined by a particular device parameter or multiple device parameters; and
comparing the vector associated with the second computing device to one or more corresponding vectors generated for one or more computing devices of the plurality of computing devices based on the plurality of sets of device parameters in the plurality of diagnostic reports.

5. The method of claim 4, wherein the comparing of the first set of one or more device parameters to the plurality of sets of device parameters further comprises:
identifying a device category of the second computing device based on the first set of one or more device parameters, wherein how the vector associated with the second computing device is generated depends on the identified device category.

6. The method of claim 5, wherein the comparing of the first set of one or more device parameters to the plurality of sets of one or more device parameters further comprises:
determining whether one or more of a collection of one or more vectors associated with the same device category as the second computing device match the vector associated with the second computing device according to predefined criteria; and
in response to one or more matches according to the predefined criteria being found, selecting one or more diagnostic reports associated with said one or more matching vectors as a classification cluster for the second computing device, wherein the method further comprises:
performing, in response to the selecting of the classification cluster, the predicting of the results of the one or more diagnostic tests based on the classification cluster.

7. The method of claim 4, wherein the comparing of any vector associated with the second computing device to the one or more corresponding vectors generated based on the plurality of diagnostic reports further comprises calculating a value of a distance metric quantifying a difference between the vector of the second computing device and the one or more corresponding vectors and the pre-defined criteria comprise a pre-defined upper threshold for the distance metric.

8. The method according to claim 1, wherein the comparing of the first set of one or more device parameters to the plurality of sets of one or more device parameters further comprises:
determining, for each of one or more components of the second computing device, a second set of one or more component-specific device parameters based on the first set of one or more device parameters received from the first computing device;
searching for matches for one or more second sets of one or more component-specific device parameters from the diagnostic report database;
in response finding at least one match for at least one second set of one or more component-specific device parameters, selecting, for each second set of one or more component-specific device parameters for which at least one match was found, one or more diagnostic reports associated with the one or more corresponding matches as a component-specific classification cluster for said component, wherein the method further comprises:
performing, in response to the selecting of one or more component-specific classification clusters for one or more components, the predicting of the results of one or more diagnostic test(s) based on the one or more component-specific classification clusters.

9. The method according to claim 1, wherein the comparing of the first set of one or more device parameters to the plurality of sets of one or more device parameters further comprises:
identifying, for each of one or more components of the second computing device, a component category based on the first set of one or more device parameters;
generating, for each of the one or more components of the second computing device, a component-specific vector based on the first set of one or more device parameters and the one or more identified component categories, wherein each element of each component-specific vector has a numerical value representing a particular feature of said component of the second computing device defined by a particular device parameter or multiple device parameters; and
comparing each component-specific vector associated with the second computing device to one or more corresponding component-specific vectors generated for one or more computing devices of the plurality of computing devices based on the plurality of sets of one or more device parameters in the plurality of diagnostic reports.

10. The method of claim 9, wherein the comparing of the first set of one or more device parameters to the plurality of sets of one or more device parameters further comprises:
determining whether one or more of the one or more component-specific vectors generated for the one or more computing devices match the one of one or more component-specific vectors of the second computing device according to pre-defined criteria; and
in response to one or more matches according to the pre-defined criteria being found, selecting, for each of the one or more components of the second computing device, one or more diagnostic reports associated with said one or more matching component-specific vectors as a component-specific classification cluster, wherein the method further comprises:

performing, in response to the selecting of one or more component-specific classification clusters, the predicting of the results of the one or more diagnostic tests component-specifically based on diagnostic reports in the one or more component-specific classification clusters.

11. The method according to claim 1, wherein the first set of one or more device parameters retrieved by the first computing device and/or each set of one or more device parameters comprised in each diagnostic report comprise information on one or more of a manufacturer of a corresponding computing device, a model of the corresponding computing device, operating system of the corresponding computing device and at least a part of a log history of the corresponding computing device.

12. The method according to claim 1, wherein the first set of one or more device parameters retrieved by the first computing device and/or each set of one or more device parameters comprised in each diagnostic report comprise at least one of an age of a corresponding computing device or an effective age of the corresponding computing device.

13. A remote computing system comprising means for performing a method according to the following steps:

maintaining, in a diagnostic report database, one or more diagnostic reports on each of a plurality of computing devices, wherein each diagnostic report comprises results of one or more diagnostic tests performed on a computing device of the plurality of computing devices and a set of one or more device parameters characterizing said computing device;

receiving, by a remote computing system, a first set of one or more device parameters characterizing a second computing device via a communications network from a first computing device;

comparing, by the remote computing system, in response to the receiving, the first set of one or more device parameters to a plurality of sets of device parameters in a plurality of diagnostic reports maintained in the diagnostic report database to find one or more diagnostic reports corresponding to the same or similar computing devices as the second computing device;

predicting, by the remote computing system, results of one or more diagnostic tests when performed on the second computing device based on results of one or more diagnostic tests in the one or more diagnostic reports corresponding to the same or similar computing devices as the second computing device by using statistical analysis; and sending, by the remote computing system, results of the predicting to the first computing device via the communications network;

selecting, based on the results of the predicting, one or more diagnostic tests for diagnosing the second computing device; and performing the one or more selected diagnostic tests on the second computing device.

14. The remote computing system of claim 13, wherein the remote computing system is a cloud-based system and/or the diagnostic report database is a cloud-based database.

15. The remote computing system of claim 13, further comprising a non-transitory computer readable media having stored thereon instructions that, when executed by a computing device, cause the computing device to perform a method according to the steps of claim 13.

16. The remote computing system of claim 13, further comprising:

a remote computing system; and one or more first computing devices, each of the one or more first computing devices comprising means for performing:

retrieving a first set of one or more device parameters characterizing a second computing device electrically connected to a first computing device from a memory of the second computing device;

sending the first set of one or more device parameters via a communications network to the remote computing system; and displaying, in response to receiving predicted results of one or more diagnostic tests when performed on the second computing device from the remote computing system via the communications network, received information to a user via a display of the first computing device.

17. The remote computing system of claim 16, wherein the means of each of the one or more first computing devices are further configured to perform:

generating, in response to the one or more selected diagnostic tests concluding, a diagnostic report on the one or more diagnostic tests, wherein the diagnostic report on the diagnostic test comprises at least the first set of one or more device parameters and results of the one or more diagnostic tests comprising at least a diagnosis of each diagnostic test; and sending the diagnostic report to the remote computing system via the communications network.

18. The remote computing system of claim 16, wherein each of the one or more first computing devices is one of a laptop and a desktop computer and/or each second computing device electrically connected to at least one of the one or more first computing devices is a mobile device.

19. The remote computing system of claim 16, further comprising:

one or more second computing devices, wherein each second computing device comprises at least one memory and is connected electrically to one of the one or more first computing devices.

* * * * *